United States Patent
Talish et al.

[11] Patent Number: 6,165,144
[45] Date of Patent: Dec. 26, 2000

[54] APPARATUS AND METHOD FOR MOUNTING AN ULTRASOUND TRANSDUCER

[75] Inventors: Roger Talish, Hillsborough; Kenneth Urgovitch, Sr., Clifton, both of N.J.; Donald E. Krompasick, Bethlehem, Pa.; Robert Scott Ludecker, Freeport; Emery Rose, Astoria, both of N.Y.

[73] Assignee: Exogen, Inc., Piscataway, N.J.

[21] Appl. No.: 09/040,155

[22] Filed: Mar. 17, 1998

[51] Int. Cl.[7] .................................................. A61B 17/56
[52] U.S. Cl. .................................................. 601/2; 607/50
[58] Field of Search .................................... 600/439, 437, 600/459; 601/2; 607/7, 50, 51, 151, 152

[56] References Cited

U.S. PATENT DOCUMENTS

| | | |
|---|---|---|
| 4,296,753 | 10/1981 | Goudin . |
| 4,556,066 | 12/1985 | Senrow . |
| 4,947,853 | 8/1990 | Hon . |
| 5,003,965 | 4/1991 | Talish et al. . |
| 5,186,162 | 2/1993 | Talish et al. . |
| 5,211,160 | 5/1993 | Talish et al. . |
| 5,520,612 | 5/1996 | Winder et al. . |
| 5,556,372 | 9/1996 | Talish et al. . |
| 5,730,705 | 3/1998 | Talish et al. . |
| 5,904,659 | 5/1999 | Duarte et al. . |

FOREIGN PATENT DOCUMENTS 331 348 A1  9/1989  European Pat. Off. .

OTHER PUBLICATIONS

International Search Report dated Jul. 6, 1999.

*Primary Examiner*—Marvin M. Lateef
*Assistant Examiner*—Shawna J. Shaw
*Attorney, Agent, or Firm*—Bruce D. Gray; Kilpatrick Stockton

[57] ABSTRACT

An apparatus and method for mounting an ultrasound transducer head module. The apparatus includes an insert having an axial bore therein and a plurality of tabs extending radially therefrom. A spacer is provided and configured to fit within a void in a cast. The spacer has a hole therein to insertably receive the insert. An ultrasound transmission-enhancing medium is positioned within the hole in the spacer and adjacent a treatment location. The ultrasound treatment head module is then positioned within the insert and means for biasing it toward the ultrasound transmission-enhancing medium is provided. A strap may be provided to secure the apparatus adjacent a body portion to be treated, with or without the existence of a cast.

28 Claims, 18 Drawing Sheets

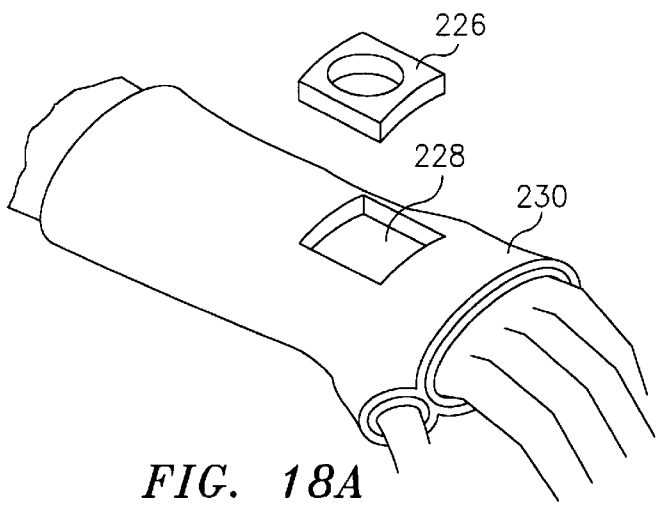
FIG. 18A
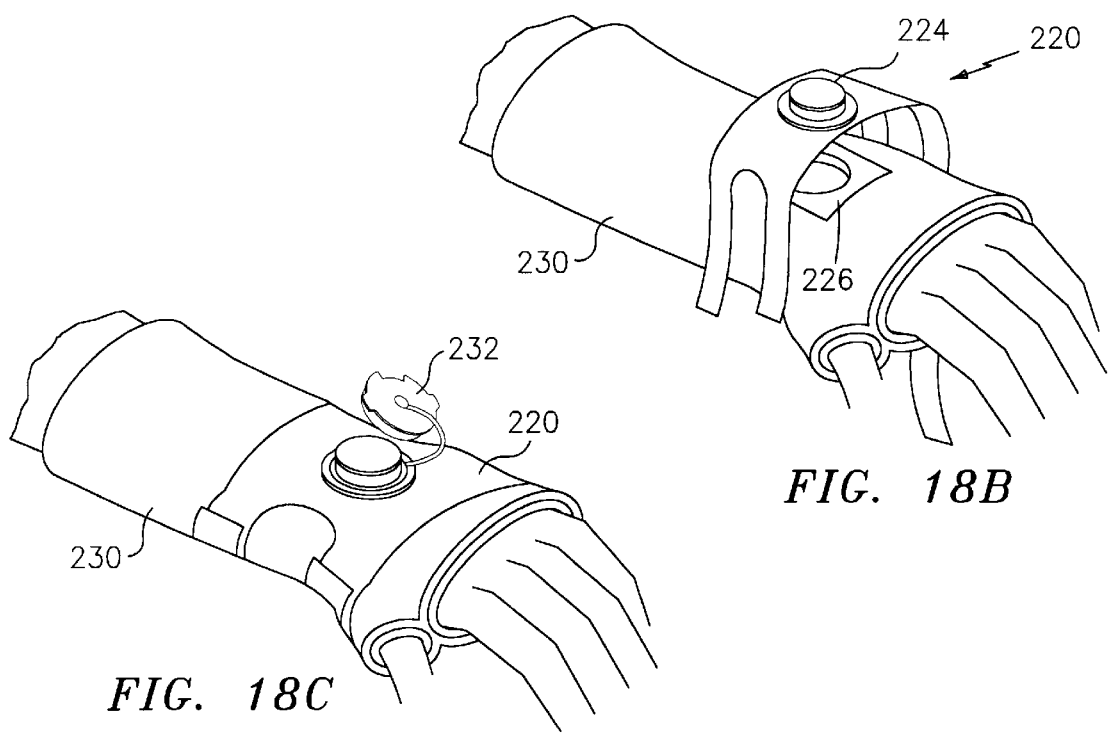
FIG. 18B
FIG. 18C
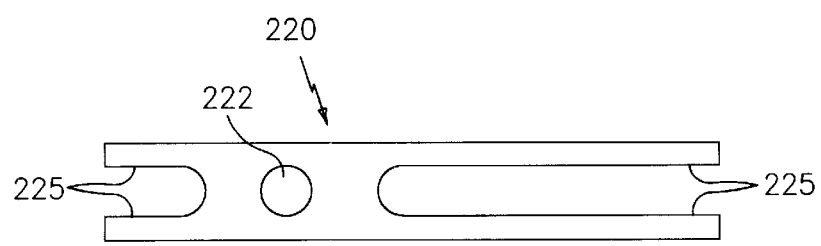
FIG. 19

APPARATUS AND METHOD FOR MOUNTING AN ULTRASOUND TRANSDUCER

BACKGROUND OF THE INVENTION

1. Field of the Invention

The present invention relates to a method and apparatus for mounting an ultrasound transducer. More particularly, the present invention relates to an apparatus for mounting an ultrasound transducer in a cast which protects the patient and transducer head module from adverse affects due to external impacts, and a method of installing the apparatus for mounting the ultrasound transducer.

2. Description of the Related Art

The use of ultrasound to therapeutically treat musculoskeletal injuries is known. Impinging ultrasonic pulses having appropriate parameters, e.g., frequency, pulse repetition, and amplitude, for suitable periods of time and at a proper external location adjacent to a bone injury has been determined to accelerate the natural healing of, for example, bone breaks and fractures and to treat osteoporosis. For patients with reduced healing capacity, such as elderly persons with osteoporosis, ultrasonic therapy may promote healing of bone injuries which would otherwise require prosthetic replacement or leave the patient permanently disabled.

U.S. Pat. Nos. 5,003,965 and 5,186,162 both to Talish and Lifshey ("Talish '965" and "Talish '162", respectively) and U.S. Pat. No. 5,520,612 to Winder et al. describe an ultrasonic delivery system where the RF generator and transducer are both part of a modular applicator unit that is placed at the skin location. The signals controlling the duration of ultrasonic pulses and the pulse repetition frequency are generated apart from the applicator unit. Talish '965 and Talish '162 also describe fixture apparatus for attaching the applicator unit so that the operative surface is adjacent the skin location. In Talish '965 and Talish '162, the skin is surrounded by a cast, while in U.S. Pat. No. 5,211,160 to Talish and Lifshey ("Talish '160") fixture apparatus is described for mounting on uncovered body parts (i.e., without a cast or other medical wrapping).

In many instances, the patient receiving ultrasound therapy treatment is mobile. A transducer head module may be mounted on the patient remote from a stationary ultrasound generator, or portable ultrasound generating apparatus may be carried by the patient as disclosed, for example, in U.S. Pat. No. 5,556,372 to Talish et al. The transducer head module is therefore increasingly more prone to external impacts which may damage the module or adversely affect the treatment efficiency. Thus, while the systems described in the prior art disclose typical therapeutic ultrasound method and apparatus, they do not disclose a method and apparatus for mounting an ultrasound transducer which protects the transducer head module and the patient.

Another problem associated with the prior art transducer mounting apparatus becomes apparent to physicians during the installation of the apparatus. Typically, a cast will be mounted on the patient prior to the time that the decision is made to administer ultrasound therapy. Therefore, the physician is required to cut a hole in the existing cast to accommodate placement of an ultrasound transducer head module adjacent a body portion of a patient requiring treatment. Since more transducer head modules are circular, a corresponding circular hole is required in the cast. However, physicians are commonly equipped with a tool having a blade which may be adjusted to limit penetration to the depth of the cast to cut a square or rectangular void in the cast. Moreover, it is inefficient to require the physician to be concerned with the precision with which the void is made in the cast. Therefore, a need exists for an apparatus which can be placed within a void in a cast and convert the square or rectangular void to a circular hole for receiving an ultrasound transducer head module which is also adaptable and versatile to minimize a precision associated with the dimensions of the void.

Alternatively, the physician may know, at the time the injury occurs, that ultrasound therapy is likely a preferred future treatment. However, the installation of a spacer which creates a void in the cast has heretofor been delayed until a period of time has elapsed such that the danger of swelling around the affected injury site has transpired, since it has been determined that the skin within the void is prone to window edema (especially during the swelling period). Therefore, a need exists for an apparatus which will allow the surgeon to install an insert in the cast at the time of injury which will insertably receive an ultrasound transducer treatment head module and also prevent window edema when the module is not in place.

Additionally, conventional transducer mounting apparatus is often bulky and cumbersome to the patient, especially when the apparatus is located on a portion of the patient's body which is typically covered by clothing. Thus, a need exists for an apparatus which has a low profile when mounted on the patient to facilitate comfort to the patient while the apparatus is mounted on a location under clothing.

SUMMARY OF THE INVENTION

It is an object of the present invention to provide an apparatus for mounting an ultrasound transducer treatment head module which overcomes these and other disadvantages of the prior art. In an embodiment thereof, the apparatus includes an insert having an axial bore therein and a plurality of tabs extending radially therefrom. When the treatment location is beneath a cast worn by the patient, a spacer having a periphery corresponding to a hole in the cast is placed therein. The spacer preferably has a hole for receiving the insert. An ultrasound transmission-enhancing medium is positioned within the hole in the spacer and adjacent to a treatment location. After the ultrasound treatment head module is positioned within the insert, means for biasing the module toward the ultrasound transmission-enhancing medium is provided.

It is another object of the present invention to provide an apparatus for mounting an ultrasound transducer treatment head module adjacent to a body portion requiring treatment that is not encased in a cast. This embodiment includes an insert member having an axial bore therein, an ultrasound transmission-enhancing medium positioned within the bore of the insert and adjacent a treatment location, means for biasing the ultrasound treatment head module positioned within the insert toward the ultrasound transmission-enhancing medium, and means removably engaging the apparatus with the treatment location.

Yet another object of the present invention is to provide a method for mounting an ultrasound transducer head module. The method includes the steps of cutting an opening in a cast of a patient adjacent a body portion to receive treatment, placing a spacer having a hole therein into the opening of the cast, placing an insert having a plurality of radially extending tabs at least partially into the hole in the spacer, weaving strips of cast material between the plurality of radially extending tabs or flange to secure the insert within the opening in the cast, placing an ultrasound transmission-enhancing medium into the insert, placing an ultrasound transducer head module into the insert, placing a cover over the ultrasound transducer head module and urgingly biasing the ultrasound transducer head module toward the body portion to receive treatment.

It is still another object of the present invention to provide an apparatus for mounting an ultrasound transducer treatment head module adjacent to a portion of the patient's body requiring treatment, wherein the apparatus is advantageously designed to account for ergonomic considerations. For example, the apparatus of the present invention requires a smaller hole to be cut in a cast and it doesn't project out as far from the patient's body as do conventional apparatus for mounting an ultrasound transducer treatment head module.

These and other objects, features and advantages of the present invention will become apparent from the following detailed description of illustrative embodiments, which is to be read in connection with the accompanying drawings.

BRIEF DESCRIPTION OF THE DRAWINGS

For a better understanding of the invention, reference is made to the following description of exemplary embodiments thereof, and to the accompanying drawings, wherein:

FIGS. 18A–C are perspective views illustrating a system for mounting an ultrasound transducer receiving apparatus adjacent a treatment location in a cast;

FIG. 19 is a plan view of an alternative embodiment of a casting tape;

DETAILED DESCRIPTION OF A PREFERRED EMBODIMENT

Figure 1:
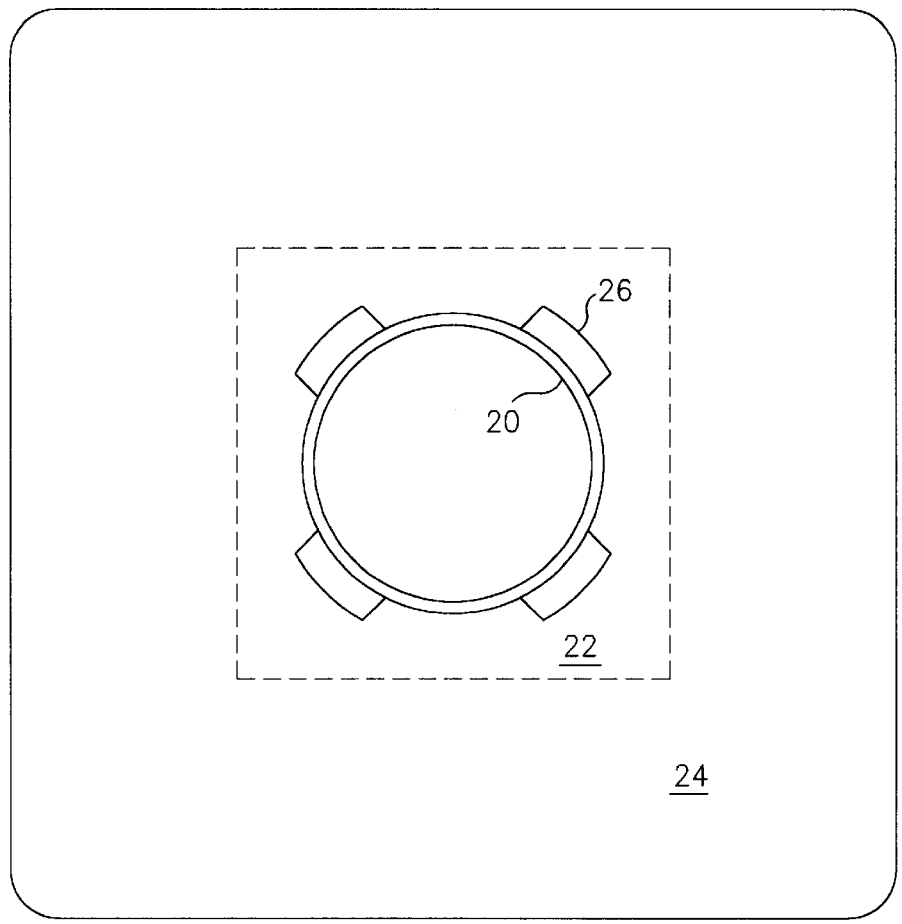
FIG. 1 is a top view of an insert within a void in a cast, in accordance with the present invention.

Referring now to the drawings in detail, and initially to FIG. 1, an insert 20 is shown, positioned within a void 22 formed in a portion of a cast 24. Void 22 has a substantially square shape and is delineated by the dashed lines. Insert 20 is shown having a substantially circular periphery and a plurality of tabs 26 extending radially therefrom. Four tabs 26 are visible in FIG. 1. Additional tabs 26 are hidden by cast material in a plane beneath the visible tabs as will become apparent in FIG. 2. Insert 20 preferably includes an axial bore within the substantially circular periphery to mount an ultrasound transducer to initiate a treatment, as will be discussed in further detail below. Insert 20 is preferably formed of polypropylene.

Figure 2:
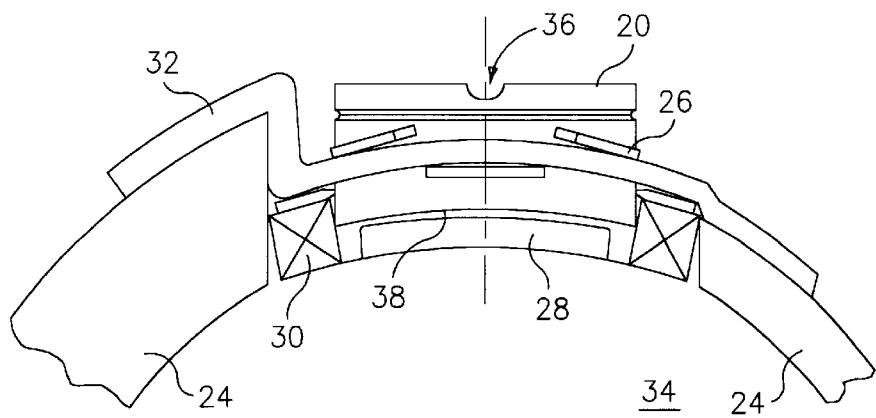
FIG. 2 is a side cross-sectional view of an insert partially secured within a void in a cast.

FIG. 2 illustrates a side cross-sectional view of insert 20 within cast 24. Prior to placing insert 20 into void 22, a spacer 30 is placed within void 22. Spacer 30 is configured to have a shape on its periphery which corresponds with the shape of void 22, and a hole in its center which corresponds to the shape of insert 20. Spacer 30 is preferably formed of a medical grade felt or a similar material which will exhibit comfortable characteristics against a body portion of a patient, and may be fabricated in a plurality of layers so that the thickness can be adjusted depending on the thickness of cast 24.

Spacer 30 maintains insert 20 at a predetermined distance from the body portion 34 of a patient, to prevent window edema or a similar injury to the patient due to uneven pressure at a casted site. As shown, insert 20 is partially inserted into the hole within spacer 30 and is supported thereon by at least one of the radially extending tabs 26. Tabs 26 contain living hinges formed by a reduction in cross-section of the tabs 26 at a proximal end adjacent the bore of insert 20 which weakens tabs 26 at the hinge point, thus allowing them to bend freely., The living hinges provide for lateral flexure of tabs 26 to enhance the ability to conform to varying angles which are a function of the anatomy of the patient. Moreover, the living hinges allow insert 20 to be articulated to correct for other angular misalignments.

Insert 20 is secured within void 22 in cast 24 by weaving strips 32 of cast material between tabs 26. A plurality of layers of cast material strips 32 are placed around insert 20 until a desired thickness is achieved. The configuration of insert 20 having tabs 26 allows the insert to be installed before or after the cast is installed. Advantageously, when the layers of cast material strips cure, insert 20 will be an integral part of the cast. Thus, any impact on the skin of the patient, which would otherwise be transferred through insert 20, will be minimized as it is absorbed by the cast.

Insert 20 may optionally include a hemispherical notch 36 in an upper end thereof to accommodate a cord extending from an ultrasound treatment head module while the module is positioned within the insert. A lower end 38 of insert 20 is preferably concave to correspond to fit a convex body portion 34 of a patient, without impacting the skin which may cause edema or a similar injury.

An ultrasound transmission-enhancing medium 28 is preferably positioned within spacer 30 adjacent a treatment location to minimize or eliminate an air gap between an ultrasound transducer head module and a treatment location. The ultrasound transmission-enhancing medium 28 is preferably a conductive gel bladder.

Figure 3:
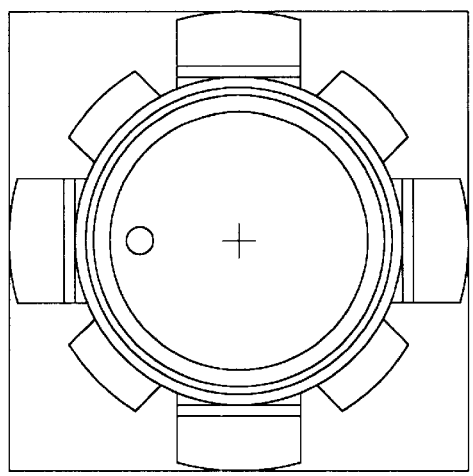
FIG. 3 is a top view of an insert having a plurality of tabs extending radially therefrom.
Figure 4:
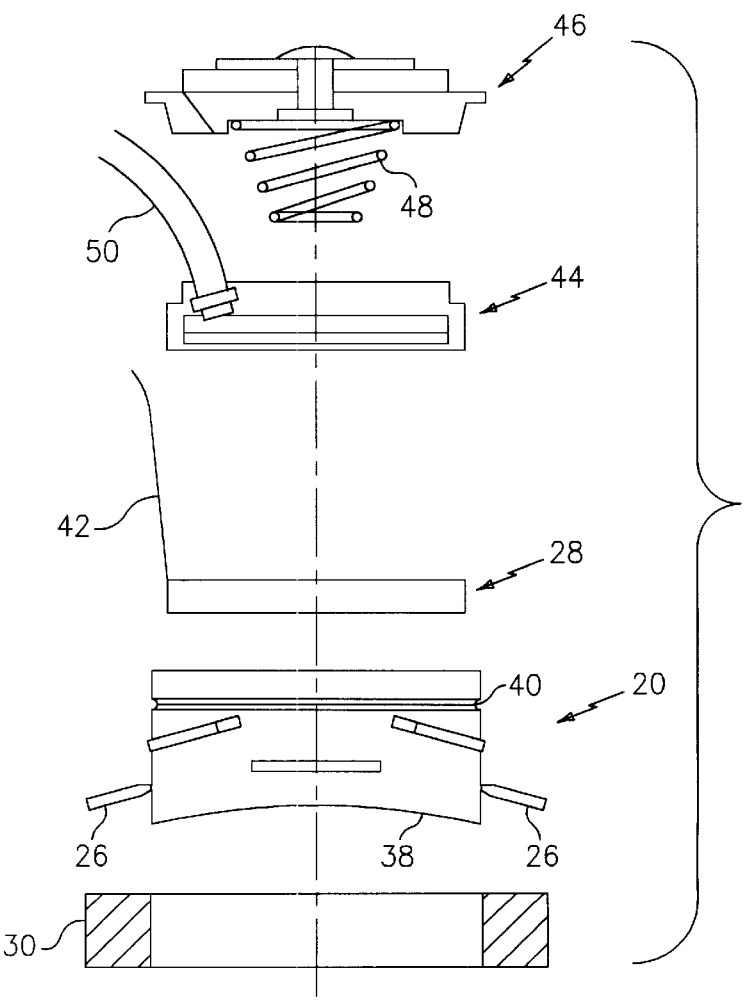
FIG. 4 is an exploded side view of an apparatus for mounting an ultrasound transducer.

The apparatus of the present invention is configured to adapt to and fit within a substantially rectangular or square-shaped void in a cast as shown in a top view thereof in FIG. 3. Advantageously, the insert 20 converts the void into a circular receptacle for receiving a corresponding circular-shaped ultrasound transducer head module. Turning now to the exploded side view in FIG. 4, and proceeding from the bottom, spacer 30 is shown in cross-section, having a hole therein configured to insertably receive insert 20. Insert 20 includes a plurality of tabs 26 and a concave lower end 38. Insert 20 preferably includes at least one circumferential groove 40 in an upper portion thereof. The purpose of the circumferential groove 40 is to enable the removal of at least one layer of insert 20 to adjust the height of insert 20 to correspond to a thickness of a cast. In a preferred embodiment of the ultrasound transmission-enhancing medium 28, a means for facilitating removal of the medium from insert 20 is provided. In this embodiment the means for facilitating removal is a tab 42 shown extending from medium 28.

An ultrasound transducer head module 44 is positioned adjacent ultrasound transmission-enhancing medium 28 within insert 20. Cord 50 connects module 44 with electronic driving circuitry. Housing 46 is then inserted in the upper portion of insert 20 to enclose the components within insert 20. A bias element 48 extends from a bottom portion of housing 46. Bias element 48 is preferably a conical helical spring. The conical helical spring is advantageously configured to fully collapse within itself and will therefore require less space within insert 20. A conical helical spring will also maintain a uniform force on ultrasound transducer head module 44 and will allow module 44 to pivot to conform to the shape of transmission-enhancing medium 28.

Figure 5:
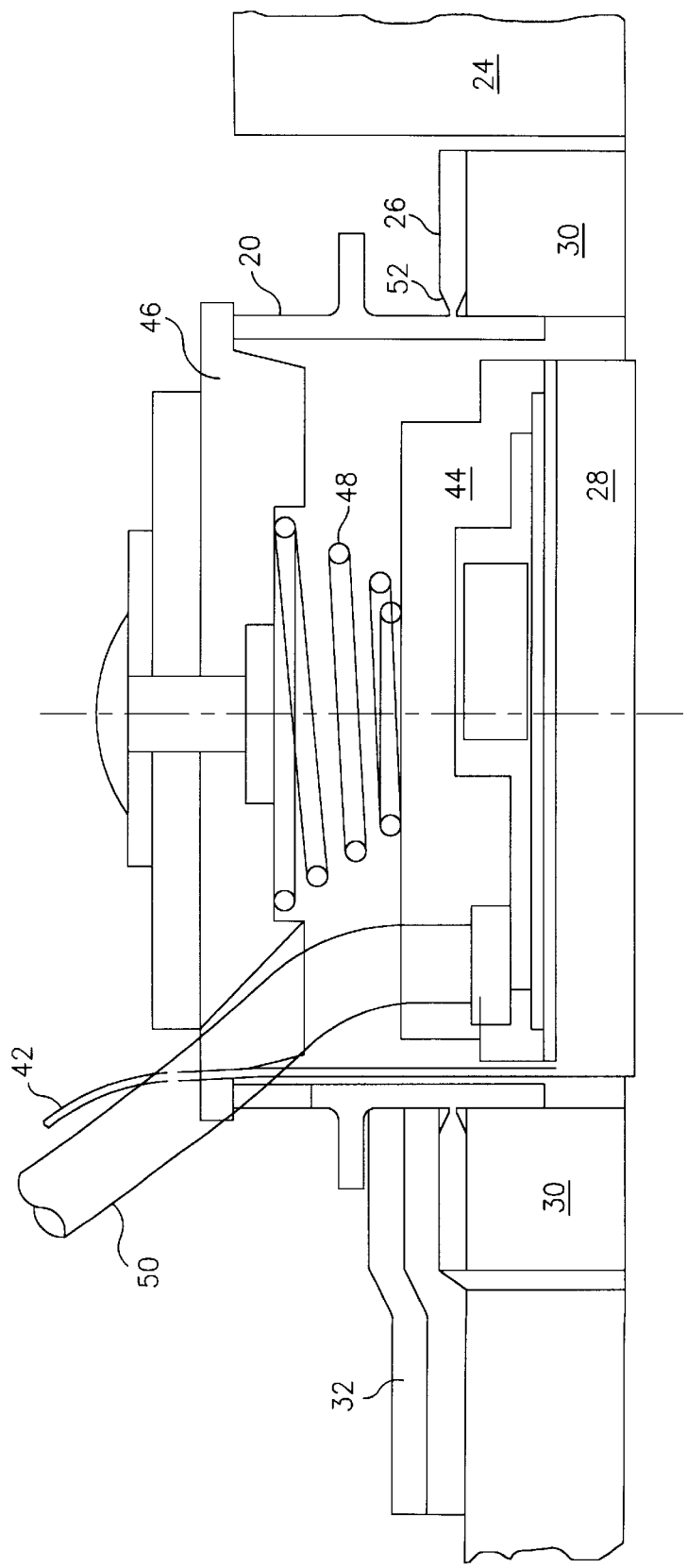
FIG. 5 is an enlarged side view of an assembled apparatus for mounting an ultrasound transducer.

FIG. 5 illustrates an enlarged side view of an assembled apparatus for mounting an ultrasound transducer in accordance with the present invention. This enlarged view illustrates the living hinge 52 on tab 26 which allows for free lateral movement. Also shown, spring 48 in its compressed state urgingly biases transducer module 44 toward ultrasound transmission-enhancing medium 28.

Figure 6:
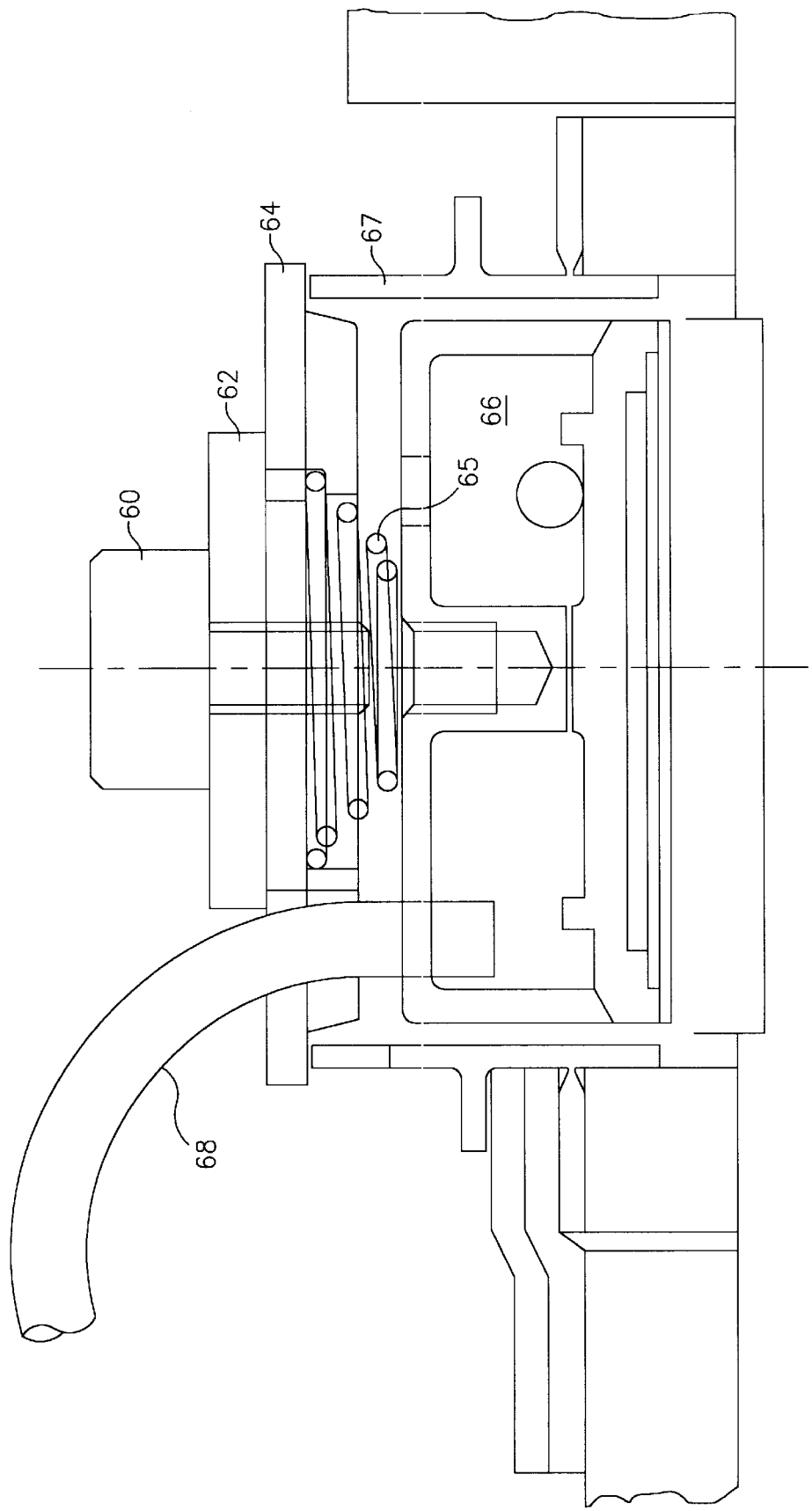
FIG. 6 is an enlarged side view of another embodiment of an assembled apparatus for mounting an ultrasound transducer.

Referring now to FIG. 6, another embodiment of the present invention is shown having a rivet 60. Rivet 60 is provided to couple a strap 62 with cover 64 when the rivet is inserted through holes therein. Strap 62 is designed to adjustably fit around a cast of a patient receiving ultrasound treatment and maintain a compressive force on spring 65 to ensure uniform and continuous pressure against ultrasound transducer head module 66 as it is positioned within insert 67. Also shown in this embodiment, cover 64 is configured to eliminate the need for the hemispherical notch 36 in insert 20 (FIG. 2), by providing an opening in cover 64 through which cord 68 passes.

It is to be noted that during the time period that the transducer head module is not in use, and therefore not within the insert, a pad must be placed within the insert to fill the void left by the transducer head module and maintain a constant pressure on the skin within the void in the cast which is equivalent to the pressure applied by the cast, to prevent edema. The pad is preferably formed of a medical grade felt similar to spacer 30. The pad may also include a hard coating or disk on an upper surface thereof to provide a rigid surface adjacent bias element 48. The hard surface will prevent the bias element form forming an imprint in the pad and will maintain a constant force on the pad via the bias element. The pad may also include a tab, similar to tab 42, to facilitate removal of the pad from the insert. Strap 62 may be used to secure the pad within the insert and to apply a force to maintain a constant pressure.

Figure 7:
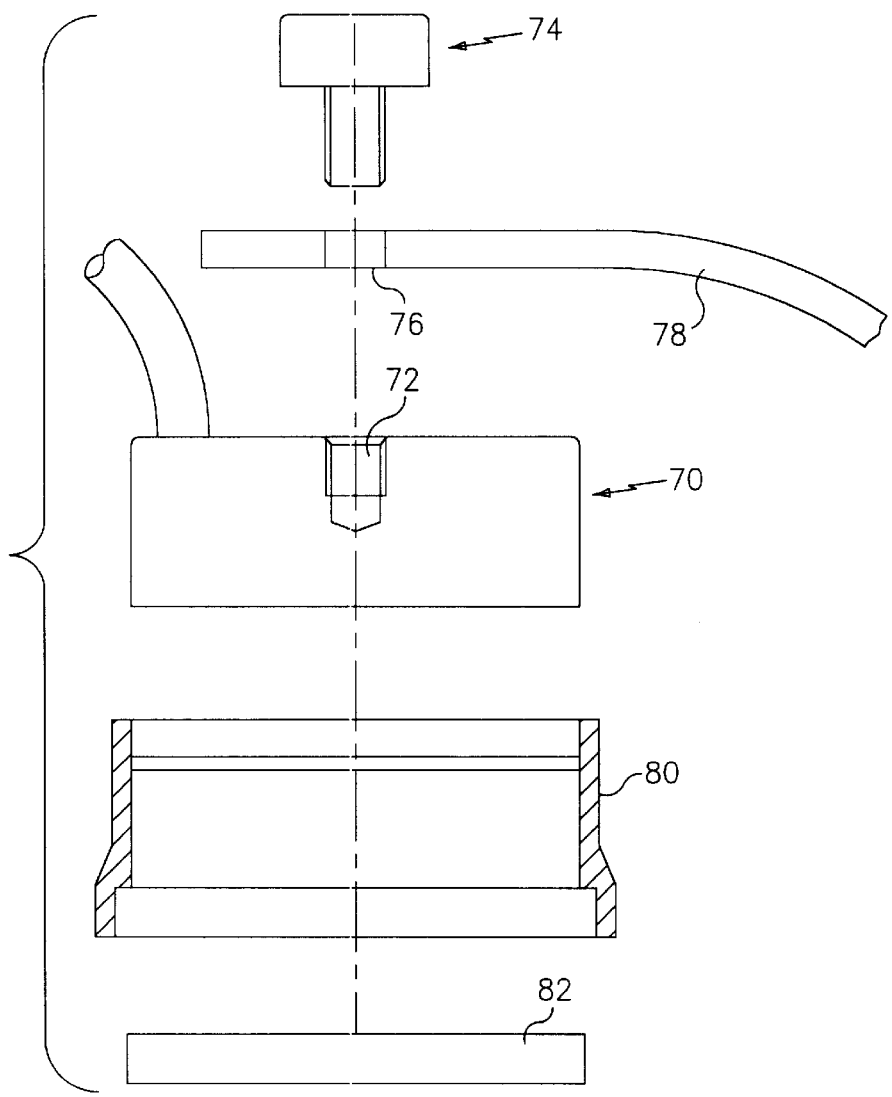
FIG. 7 is an exploded side view of another embodiment of an apparatus for mounting an ultrasound transducer.
Figure 8:
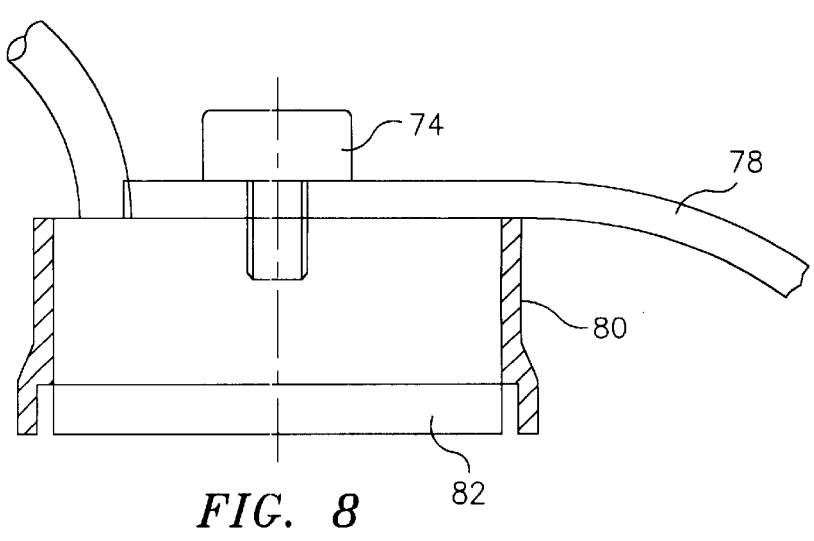
FIG. 8 is a side view of an assembled apparatus for mounting the ultrasound transducer of FIG. 7.

Referring to FIGS. 7 and 8, it is also contemplated that the apparatus may also be secured to a treatment location that does not have a cast or other medical wrapping. FIG. 7 illustrates an exploded view of such an apparatus and FIG. 8 illustrates a fully assembled view. In this embodiment, the transducer head module 70 is modified to have a hole 72 therein for receiving a rivet 74 which is inserted through a hole 76 in strap 78. Thus, when transducer head module 70 is placed within insert 80 adjacent transmission-enhancing medium 82, strap 78 and transducer head module 70 will be locked in place by means of rivet 74. Insert 80 is preferably manufactured to a height corresponding to the combined thickness of the transducer head module 70 and the transmission-enhancing medium 82.

Figure 9:
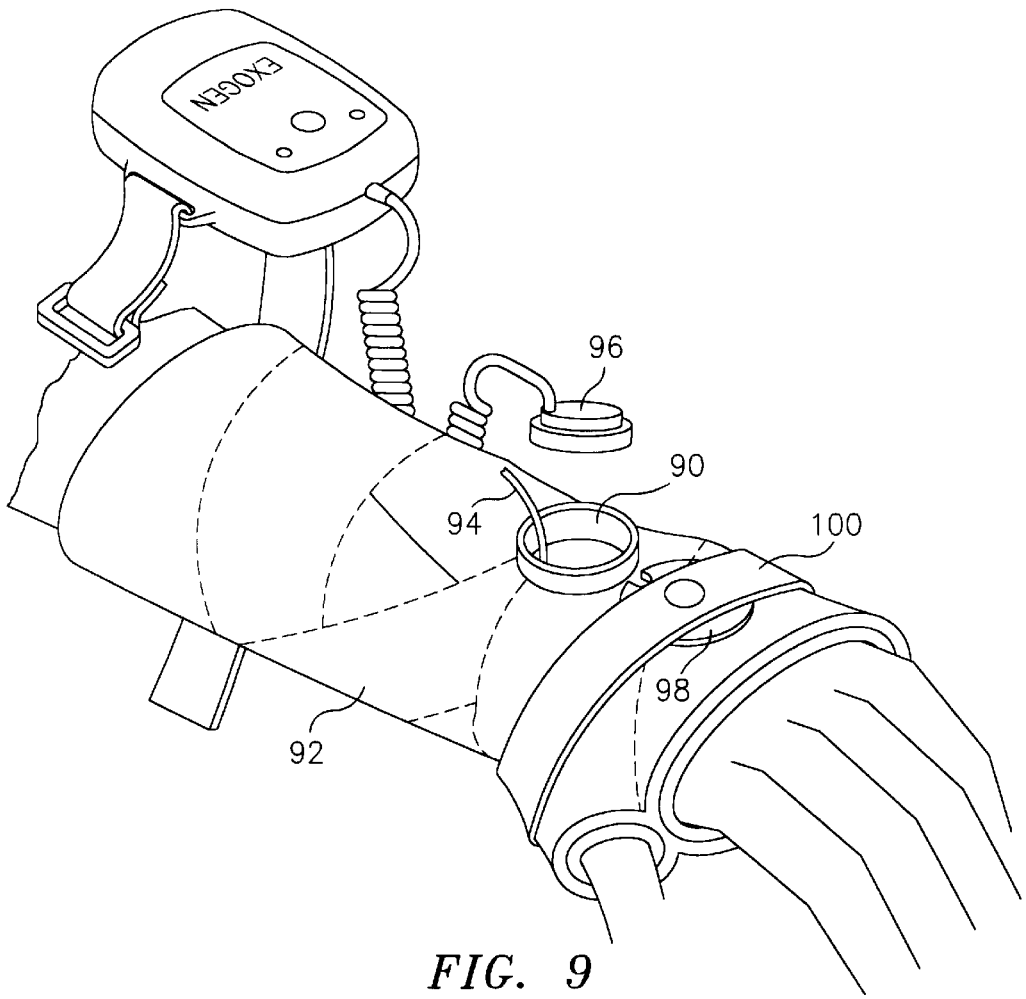
FIG. 9 is a perspective view of an insert secured in a cast ready to receive an ultrasound transducer head.
Figure 10:
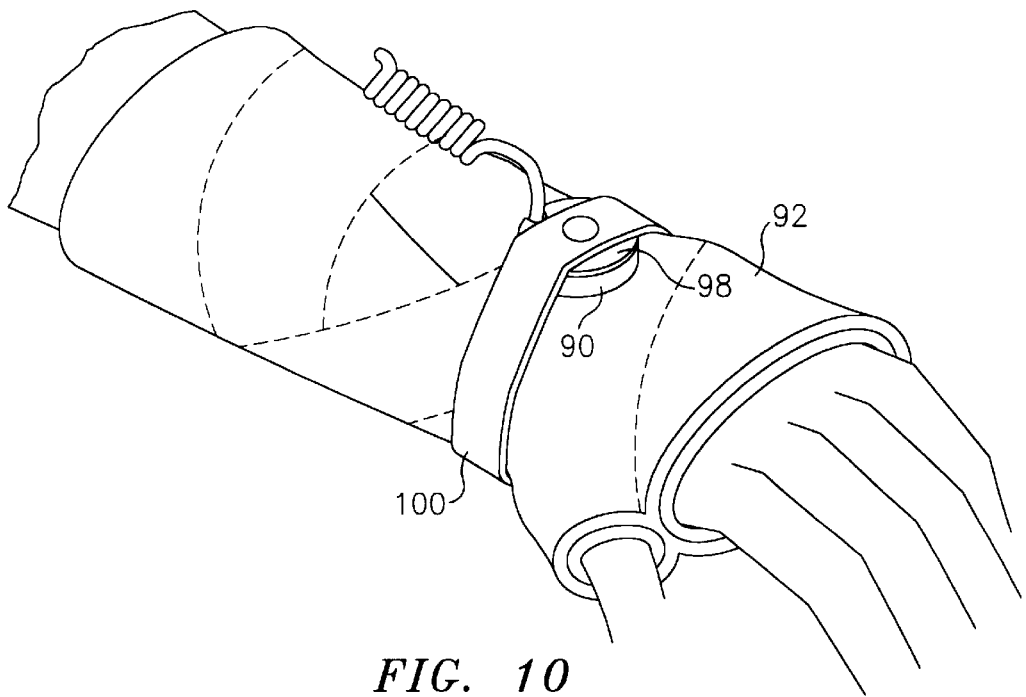
FIG. 10 is a perspective view of a fully assembled apparatus for mounting an ultrasound transducer in a cast.

Referring to FIGS. 9 and 10, insert 90 is shown secured within a cast 92 of a patient requiring ultrasound treatment. Tab 94 which is attached at its lower end to a transmission-enhancing medium is shown extending from insert 90. Following the placement of ultrasound transducer head module 96 into insert 90, cover 98 is placed over the top of insert 90 and strap 100 is adjusted to secure the entire apparatus in place.

Figure 11:
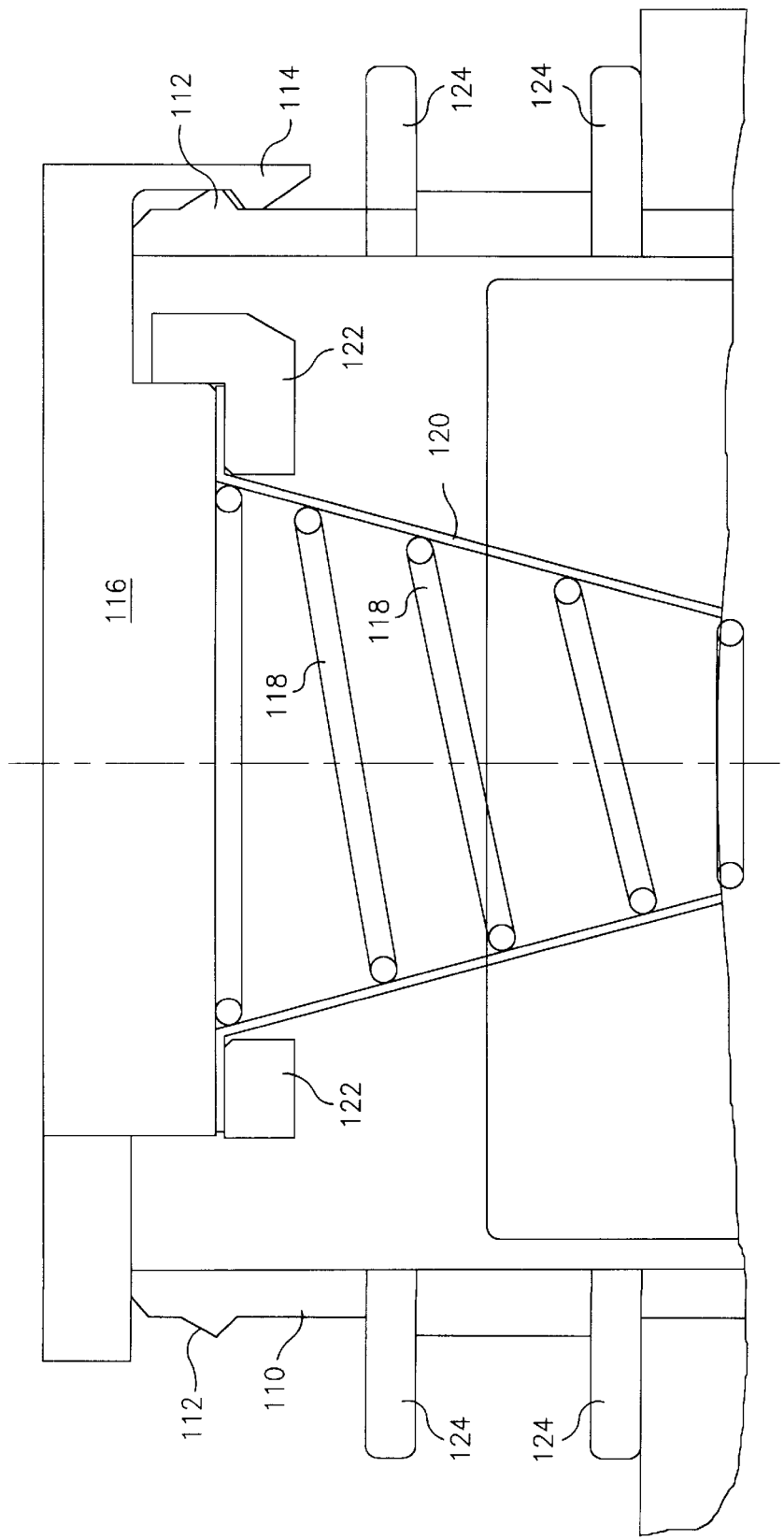
FIG. 11 is a partial enlarged side view of another embodiment of an apparatus for mounting an ultrasound transducer.
Figure 12A:
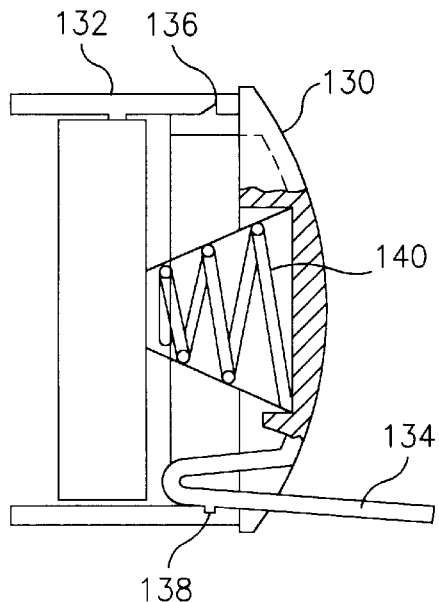
FIGS. 12A–D are various views of a cover illustrating alternative locking structure.
Figure 12B:
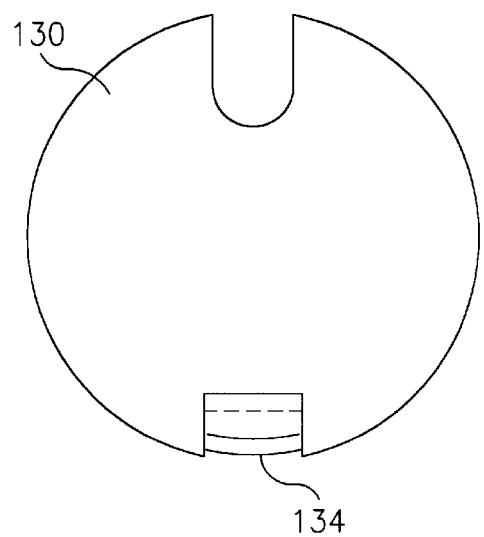
Figure 12C:
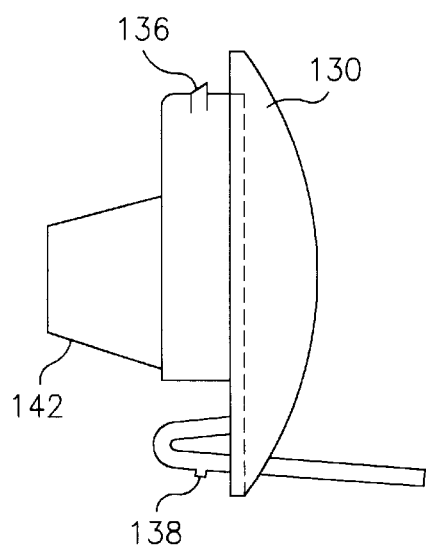
Figure 12D:
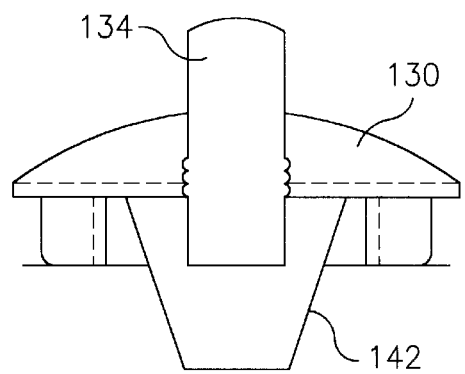

FIG. 11 illustrates an embodiment of an apparatus for mounting an ultrasound transducer which features locking structure on the outside periphery of insert 110 for retaining a transducer head module within the insert. As illustrated, the locking structure includes a circumferential ridge 112 on the outside periphery of insert 110 which is configured to engage at least one tab member 114 extending downward from an outer periphery of cover 116. Although only one tab member 114 is visible in FIG. 11, it is preferable to have three tab members extending from cover 116 and spaced 120° apart. Tab member 114 is formed of a resilient material such that it will flex outward as the ridge thereon is forced over ridge 112, and it will snap back into position after it moves beyond ridge 112. The locking structure advantageously eliminates the need for a strap to secure the cover in place, as described above with other embodiments of the presently disclosed apparatus.

Conical helical spring 118 is held in contact with a lower surface of cover 116 by resilient housing 120. Resilient housing 120 is designed to maintain spring 118 in its position under cover 116 while exhibiting resiliency corresponding to the compressive property of spring 118. Housing 120 is secured to cover 116 by lock ring 122 which may be affixed to cover 116 by epoxy or any other means known to one having ordinary skill in the art. Housing 120 is preferably formed of polyurethane having a thickness of approximately 0.01 inches.

Also illustrated in FIG. 11, are flanges 124. It is contemplated that flanges 124 may be a plurality of separate continuous circumferential flanges, a single circumferential flange having a spiral configuration around the periphery of insert 110 or at least one interrupted flange.

Figure 21:
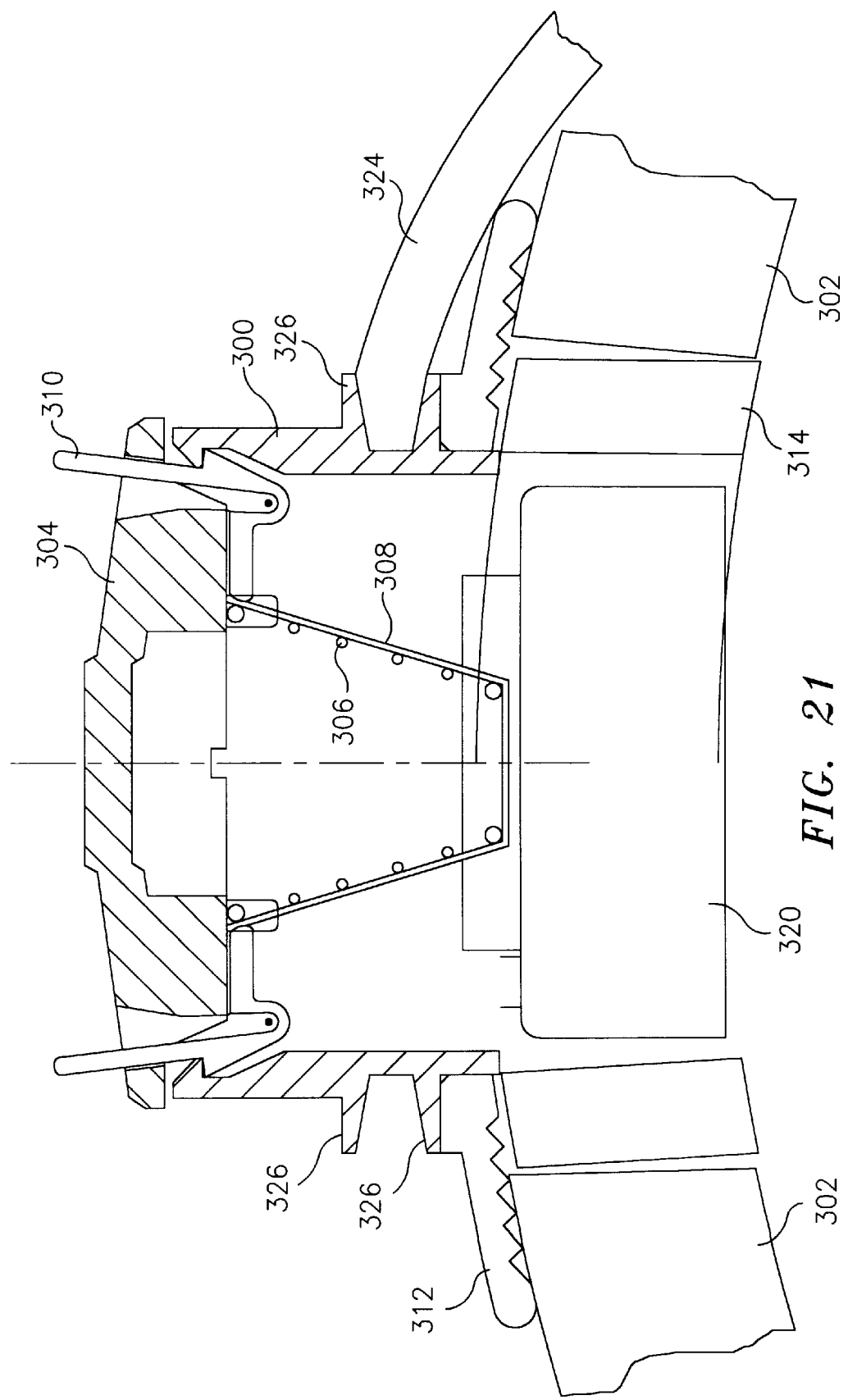
FIG. 21 is an enlarged cross-sectional side view of another embodiment of an assembled apparatus for mounting an ultrasound transducer.

FIGS. 12A–D illustrates an alternative locking structure associated with cover 130 to removably engage cover 130 with insert 132. In the cross-sectional view shown in FIG. 12A, cover 130 is illustrated locked within insert 132 by means of a hinged locking tab 134 on a first side of cover 130 and a protrusion 136 on a second side of cover 130. To remove cover 130 from insert 132, the portion of locking tab 134 which extends outwardly from cover 130 is depressed to release protrusion 138 from a groove formed on the inner surface of insert 132. Cover 130 may then be pivoted upward to disengage protrusion 136 from a corresponding groove in insert 132, and remove the cover. The disclosed locking structure advantageously eliminates the need for a strap to secure the cover in place, as described above with other embodiments of the presently disclosed apparatus. Furthermore, the configuration of locking tab 134 provides a means for easily removing the cover by a single hand of the user. Alternatively, a cover may be provided with locking structure having two locking tabs as shown in FIG. 21. The cover may be removed by depressing one locking tab, similar to the embodiment described above, or by depressing both locking tabs simultaneously.

Additionally, as an alternative to the internal locking structure illustrated in FIGS. 12A–D, FIG. 25 illustrates an embodiment of the presently disclosed mounting apparatus which employs external locking structure. As shown in this exploded view, cover 420 includes external locking tabs 422 integrally formed therewith. As cover 420 is moved in the direction of insert 424, as indicated by Arrow B, the lower portions of tabs 422 contact the circumferential lip 426 formed on the upper portion of insert 424. As cover 420 continues in this direction, tabs 422 are forced outwardly until the lower portions clear lip 426 and resiliently snap back to their original position, thereby locking cover 420 on insert 424. Cover 420 may be removed from insert 424 by depressing the upper portions of tabs 422 in a direction toward the center of cover 420, and simultaneously lifting cover 420 off insert 424.

Similar to cover 116 illustrated in FIG. 11, cover 130 includes a conical helical spring 140 which is held in contact with a lower surface of cover 130 by a resilient housing 142. Resilient housing 142 is designed to maintain spring 140 in its position under cover 130 while exhibiting resiliency corresponding to the compressive property of spring 140. Housing 142 is secured to cover 130 by a lock ring which may be affixed to cover 130 by epoxy or any other means known to one having ordinary skill in the art.

Figure 13:
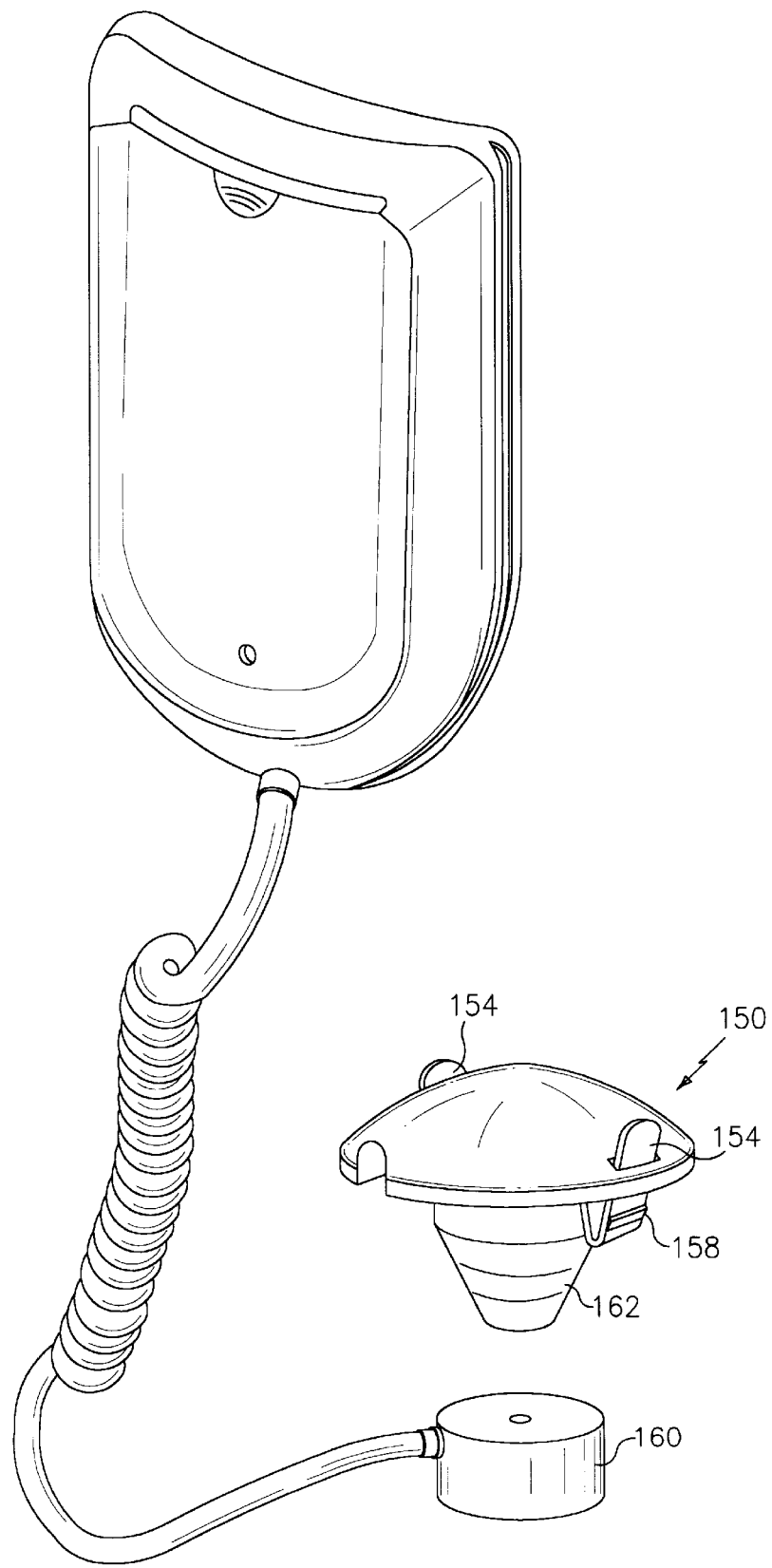
FIG. 13 is a perspective view of another embodiment of a cover with alternative locking structure.

FIG. 13 illustrates a perspective view of cover 150 having locking structure similar to that which was described above with reference to FIGS. 12A–D. Cover 150 differs from cover 130 in that cover 150 has two locking tabs 154 for locking the cover within an insert. Protrusion 158 is similarly formed on locking tab 154 to engage a groove on the inner surface of an insert. Also shown in FIG. 13 is an ultrasound treatment module with treatment head 160. Furthermore, conical helical spring 162 is connected to a lower surface of cover 150 to bias treatment head 160 in a direction toward a treatment site.

Figure 14:
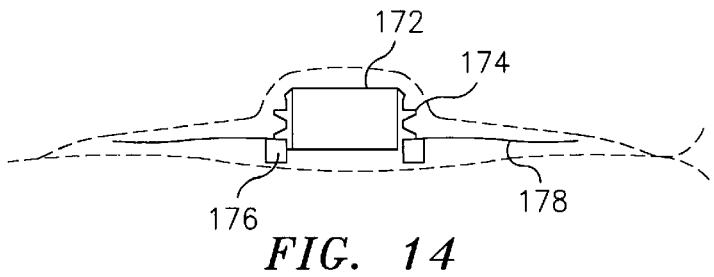
FIG. 14 is a side view in cross-section of an apparatus for the installation of an insert adjacent a treatment location prior to installing a cast thereon.

FIG. 14 illustrates an apparatus 170 for the installation of an insert adjacent a treatment location prior to installing a cast thereon for insertably receiving an ultrasound transducer treatment head. Apparatus 170 comprises an insert 172 having radial tabs 174 on an outer periphery thereof, a spacer 176 to maintain insert 172 a predetermined distance away from the skin of the patient, and padding portion 178 which wraps around the intended treatment location.

Figure 15:
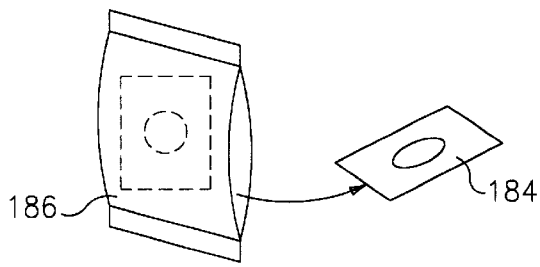
FIG. 15 is a perspective view of a piece of casting tape and a sealed package therefor.
Figure 16A:
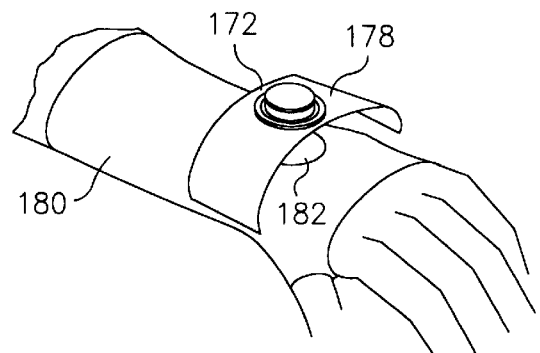
FIGS. 16A–C are perspective views illustrating a system for mounting an ultrasound transducer receiving apparatus adjacent a treatment location.
Figure 16B:
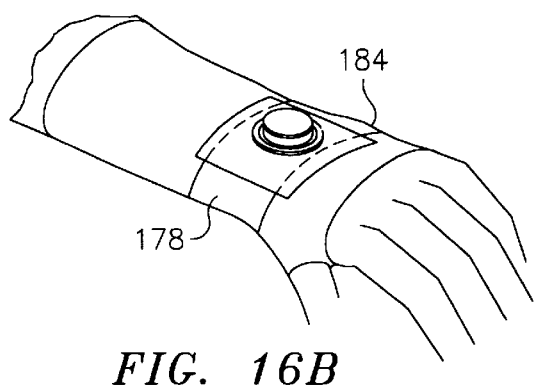
Figure 16C:
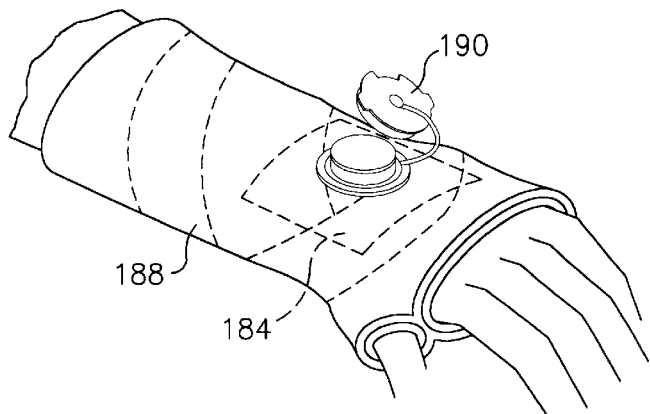

The pre-cast installation of apparatus 170 will now be described with reference to FIGS. 16A–C. Referring initially to FIG. 16A, a stocking 180 is typically placed over the portion of the patient's body over which a cast will be installed. A hole 182 is then cut in stocking 180 at the precise location for receiving ultrasound treatment. Apparatus 170 is then positioned over stocking 18 such that insert 172 is adjacent hole 182. Turning now to FIG. 16B, padding 178 is then draped around the intended treatment location and apparatus 170 is secured in place by a piece of casting tape 184. As illustrated in FIG. 15, casting tape 184 is preferably supplied having a pre-cut hole therein and is stored in a sealed package 186 to maintain sterile conditions. Casting tape 184 advantageously provides structural strength to apparatus 170 and simplifies the main cast wrapping. Referring now to FIG. 16C, apparatus 170 is shown secured within a main cast 188, ready for a cover 190 or an ultrasound transducer head module as discussed above.

Figure 17A:
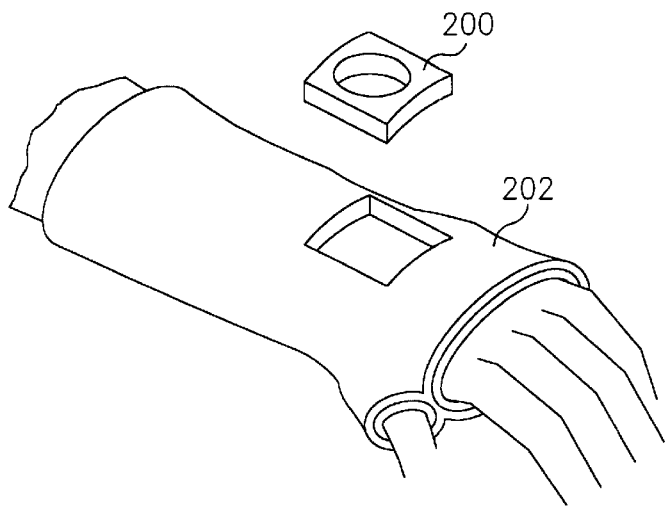
FIGS. 17A–C are perspective views illustrating a system for mounting an ultrasound transducer receiving apparatus adjacent a treatment location in a cast.
Figure 17B:
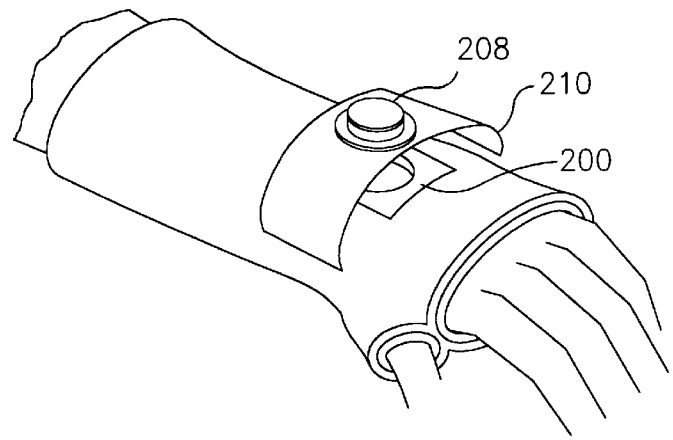
Figure 17C:
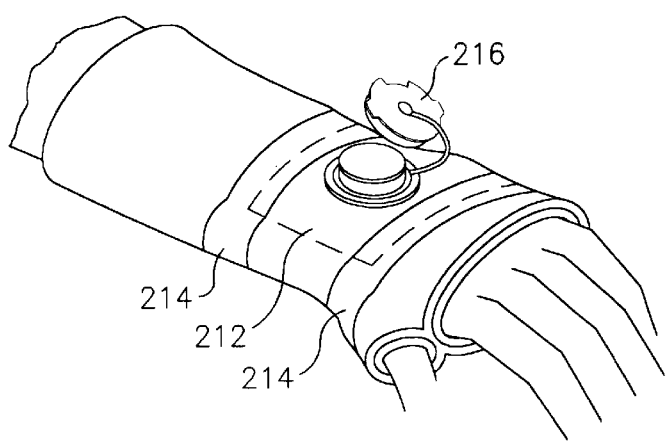

Turning now to FIG. 17A–C, a system for installing an apparatus for receiving an ultrasound treatment head module in a cast which has already been installed about a treatment location is illustrated. As shown in FIG. 17A, a felt pad 200 is provided to be placed within a void 204 cut in a cast 202. Felt pad 200 is dimensioned corresponding to the thickness of cast 202. Advantageously, felt pad 200 may initially be used as a template for cutting void 204 in cast 202. Felt pad 200 is then installed within void 204. Referring to FIG. 17B, felt pad 200 is shown within void 204 adjacent a treatment location on a patient and apparatus 206 is positioned such that insert 208 fits within the hole in felt pad 200. Padding 210 is then draped around cast 202. Turning now to FIG. 17C, apparatus 206 is then secured in place with a precut piece of casting tape 212 which is configured and dimensioned to fit over insert 208. Apparatus 206 and tape 212 may then be further secured in place by strips of 1" wide casting tape 214. A cover 216 or ultrasound transducer may then be placed in insert 208.

FIGS. 18A–C illustrate a system for installing an apparatus for receiving an ultrasound treatment head module in a cast while utilizing an alternative embodiment to the precut piece of casting tape 212 described above. The alternative embodiment is illustrated in FIG. 19 and is designated as numeral 220. Casting tape 220 has a hole 222 formed therein which is dimensioned to fit over an insert 224, and further includes a pair of legs 225 extending laterally from either side.

Similar to the system described above with reference to FIGS. 17A–C, the system illustrated in FIGS. 18A–C begin with using a felt pad 226 as a template to cut a void 228 in a cast 230. Next, the void is cut and felt pad 226 is placed within void 228, and an apparatus including insert 224 for insertably receiving a transducer head module is draped over cast 230 such that insert 224 is positioned over a corresponding hole in felt pad 226. Finally, casting tape 220 is placed over insert 224 and legs 225 are wrapped around cast 230 to secure insert 224 in place. A cover 232 or ultrasound transducer may then be placed in insert 224.

Alternatively, instead of securing the apparatus with a piece of casting tape, the apparatus may include padding, similar to that which is shown as numeral 210 in FIG. 17B, wherein the padding is configured in a shape similar to casting tape 220. The legs of the padding may then include a means for fixing the apparatus securely in position; such as, for example, VELCRO™, adhesive, plastic ties or a buckle.

Figure 20A:
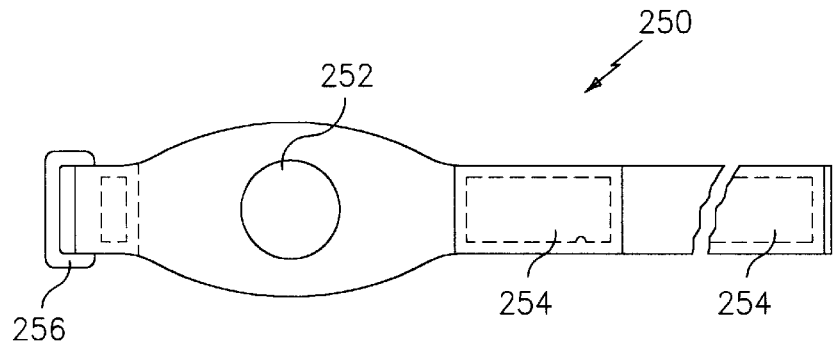
FIGS. 20A–C are plan views of alternative embodiments of a strap for securing the apparatus for mounting an ultrasound transducer adjacent to a portion of the patient's body requiring treatment.
Figure 20B:
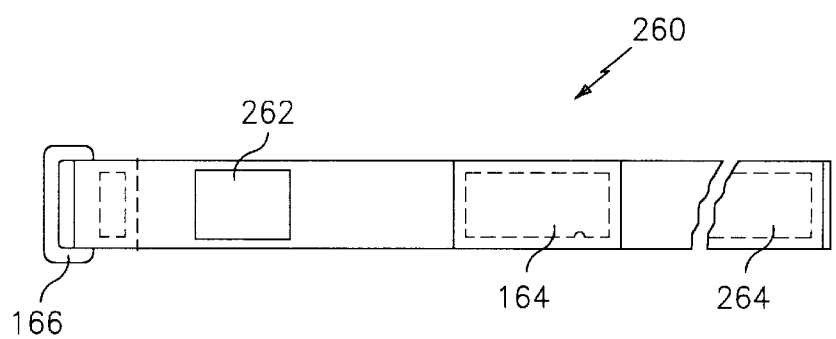
Figure 20C:
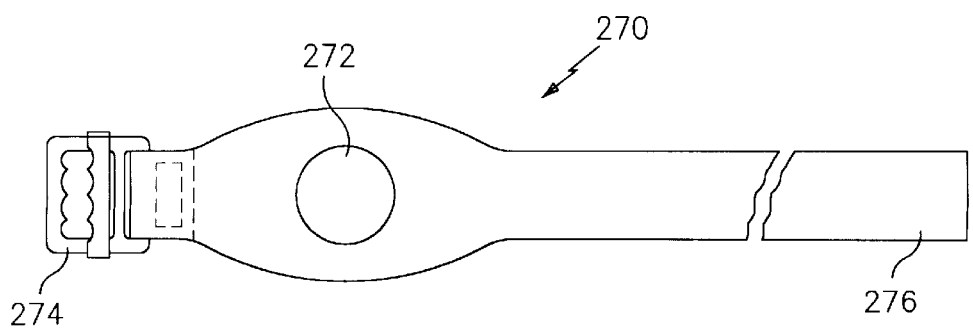

As an alternative to securing the apparatus with the above-described casting tape, straps 250, 260 and 270 illustrated in FIGS. 20A–C, respectively, may be utilized therefor. Straps 250, 260 and 270 are preferably formed of a Neoprene material and are preferably 3/32 inches thick and twenty-eight inches long (although they may be made longer, shorter, thicker or narrower to suit a particular requirement). Each of straps 250 and 270 define a hole 252 and 272, respectively, which is configured and dimensioned to stretch and fit around the outer periphery-of an insert. As illustrated in FIGS. 20A and B, straps 250 and 260 each include two VELCRO™ hook patches 254 and 264, respectively, attached thereto. Patches 254 and 264 are configured to be compatible with loops formed in the neoprene strap to thereby facilitate virtually unlimited adjustability of the strap as it is placed around the patient. A single loop is attached to an end of strap 250. As strap 250 is placed over the insert it is secured in place by inserting the end opposite loop 256 through loop 256, pulling it taut and pressing patches 254 against the VELCRO™ to removably secure strap 250 in place. Strap 260 is secured in a similar fashion. Strap 260 does not include a hole dimensioned to fit around the outer periphery of an insert. Rather, strap 260 includes an additional VELCRO™ patch 262 for attachment to a mating patch which is secured to a surface of an ultrasound transducer. Strap 270, illustrated in FIG. 20C, is alternatively provided with a slider bar loop 274 configuration to insertably receive end portion 276. Thus, to secure strap 272 around the patient's body, end 276 is woven through slider bar loop 274 and pulled taut as required. The strap is then held in place between the teeth on the slider bar and loop.

Referring now to FIG. 21, a side cross-sectional view of insert 300 is illustrated within cast 302. Prior to placing insert 300 into a void in cast 302, a spacer 314 is placed within the void. Spacer 314 is configured to have a shape on its periphery which corresponds with the shape of a void in the cast, and a hole in its center which corresponds to the shape of insert 300. Spacer 314 is preferably formed of a medical grade felt or similar material which will exhibit comfortable characteristics against a body portion of a patient, and may be fabricated in a plurality of layers so that the thickness can be adjusted depending on the thickness of cast 302.

Spacer 314 maintains insert 300 at a predetermined distance from the body portion of a patent. To prevent window edema or a similar injury to the patient, due to uneven pressure at a casted site, snap plate 312, which will be discussed in further detail below, is placed over spacer 314 and defines a hole therein which is dimensioned corresponding to the hole in spacer 314. Snap plate 312 is configured to bias insert 300 away from the patient's body and to flex to prevent damage to the patient in case the insert is subject to an external force.

Insert 300 is secured within the void in cast 302 by weaving strips 324 of cast material between tabs 326. A plurality of layers of cast material strips 324 are placed around insert 300 until a desired thickness is achieved. The configuration of insert 300 having tabs 326 allows the insert to be installed before or after the cast is installed. Advantageously, when the layers of cast material strips cure, insert 300 will be an integral part of the cast. Thus, any impact on the skin of the patient, which would otherwise be transferred through insert 300, will be minimized as it is absorbed by the cast.

An ultrasound transducer head module 320 may then be positioned within insert 300. Cover 304, having locking tab assembly 310, is then inserted in the upper portion of insert 300 to enclose the components within insert 300. A bias element 306 extends from a bottom portion of cover 304. Bias element 306 is preferably a conical helical spring and is held in contact with a lower surface of cover 304 by resilient housing 308.

Figure 22:
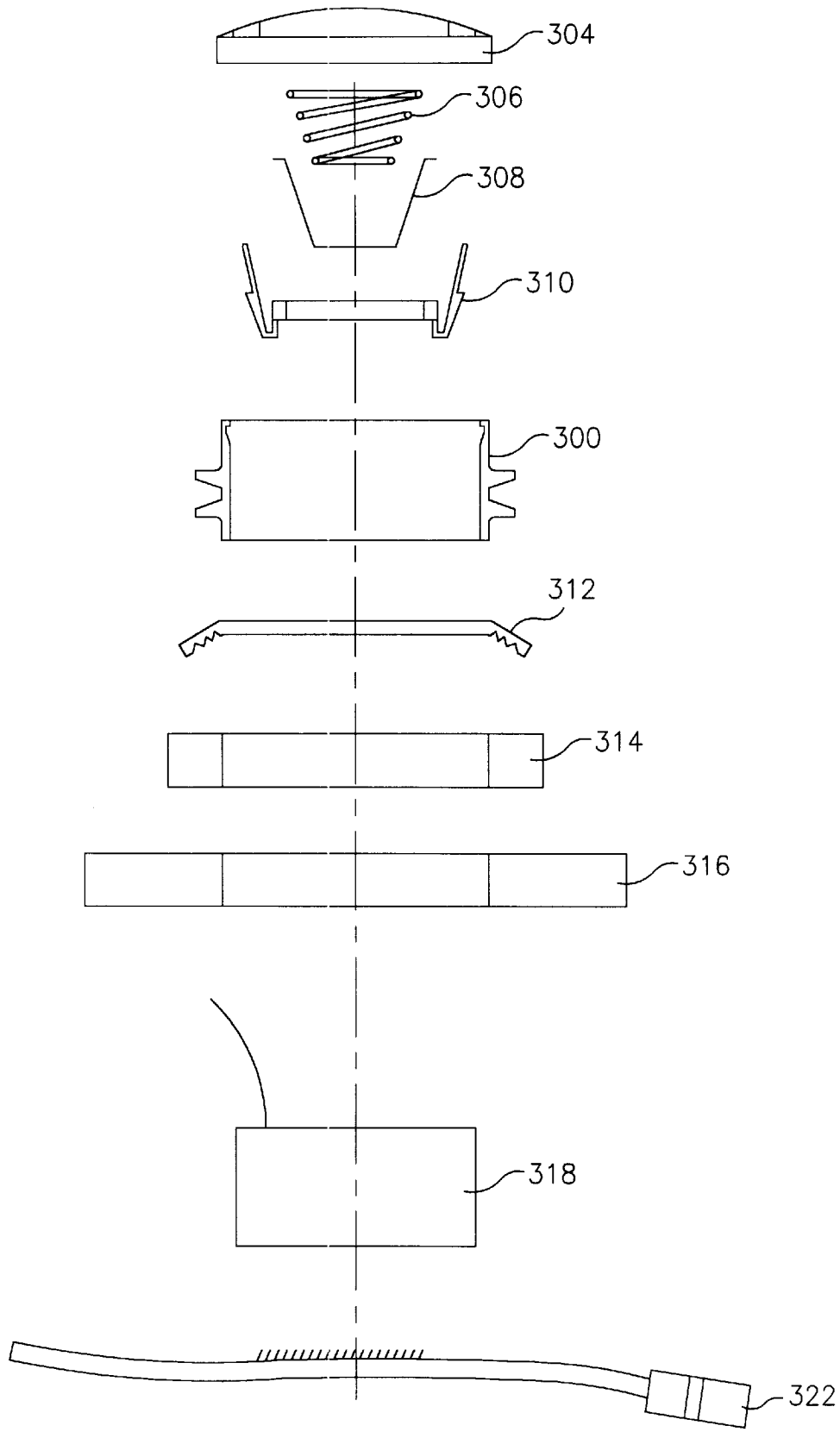
FIG. 22 is an exploded side view of the apparatus of FIG. 21.

Referring now to an exploded side view in FIG. 22, and proceeding from the bottom, a modular field reconfigurable kit is provided having components which facilitate the installation of a transducer head module adjacent a portion of a patient's body while the cast is being installed, after the cast is installed, or at a location having no cast. The kit includes a strap 322 which is primarily used in the no-cast application; a felt plug 318 which is inserted within insert 300 while the transducer head module is not in use; a foam pad 316 which is also primarily used during the no-cast application; a felt pad 314; a snap plate 312 which may alternatively be connected to insert 300; an insert 300; a locking tab assembly 310; a spring housing 308; a spring 306; and a cover 304. Advantageously, a single kit is provided which includes all of the necessary components for mounting an ultrasound transducer adjacent a portion of the patient's body, regardless of whether a cast will be installed in the future, already exists, or will not be installed at all.

Figure 23A:
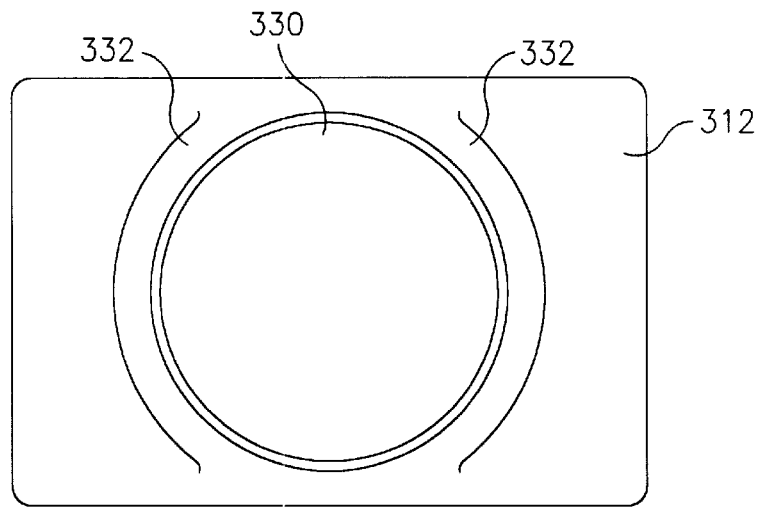
FIGS. 23A–C are top, side and bottom views of a snap plate.
Figure 23B:
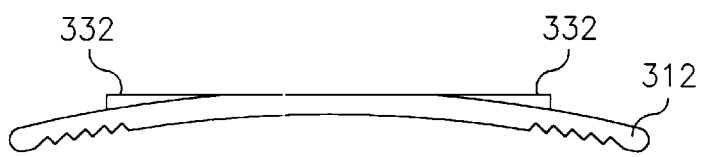
Figure 23C:
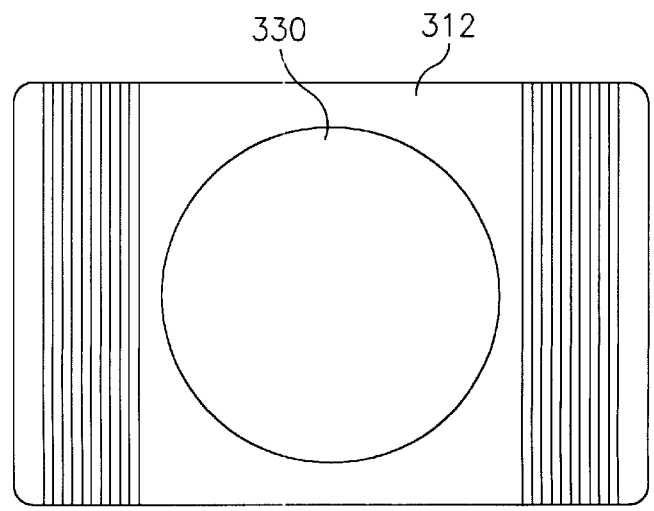

FIGS. 23A–C illustrate top, side and bottom views, respectively, of snap plate 312. Snap plate 312 defines a hole 330 therein which is dimensioned in accordance with the outside diameter of insert 300. As shown in FIGS. 23A and B, snap plate 312 includes two raised portions 332 located on either side of hole 330. The two raised portions 332 provide a flat horizontal platform for insert 300 to rest upon. As illustrated in FIG. 23B, snap plate 312 is contoured to attain a concave lower surface which will advantageously fit around a cast of a patient. The contour also gives snap plate 312 the ability to flex in response to a force exerted on insert 300 which is transmitted therethrough to an upper portion of the snap plate. As illustrated in FIGS. 23B and C, a plurality of serrations are provided on the bottom side surfaces. It is preferable that five equally spaced 90° serrations are provided to facilitate enhanced grip between the snap plate and a cast. Snap plate 312 is preferably formed of fire retardant ABS or an equivalent material.

Figure 24A:
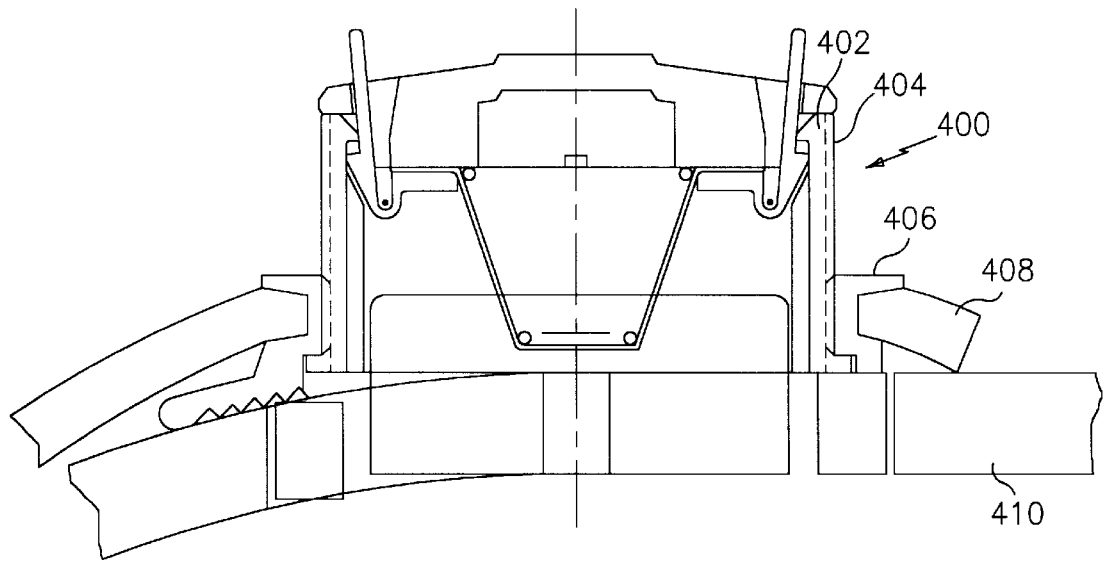
FIGS. 24A–B are side views of yet another embodiment of an apparatus for mounting an ultrasound transducer.
Figure 24B:
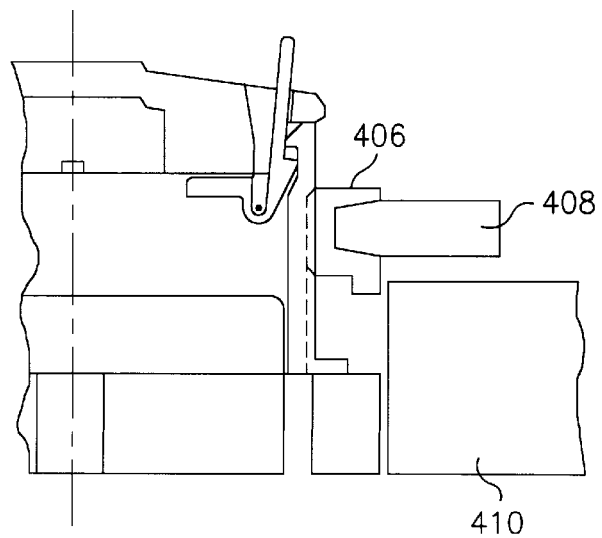
Figure 25:
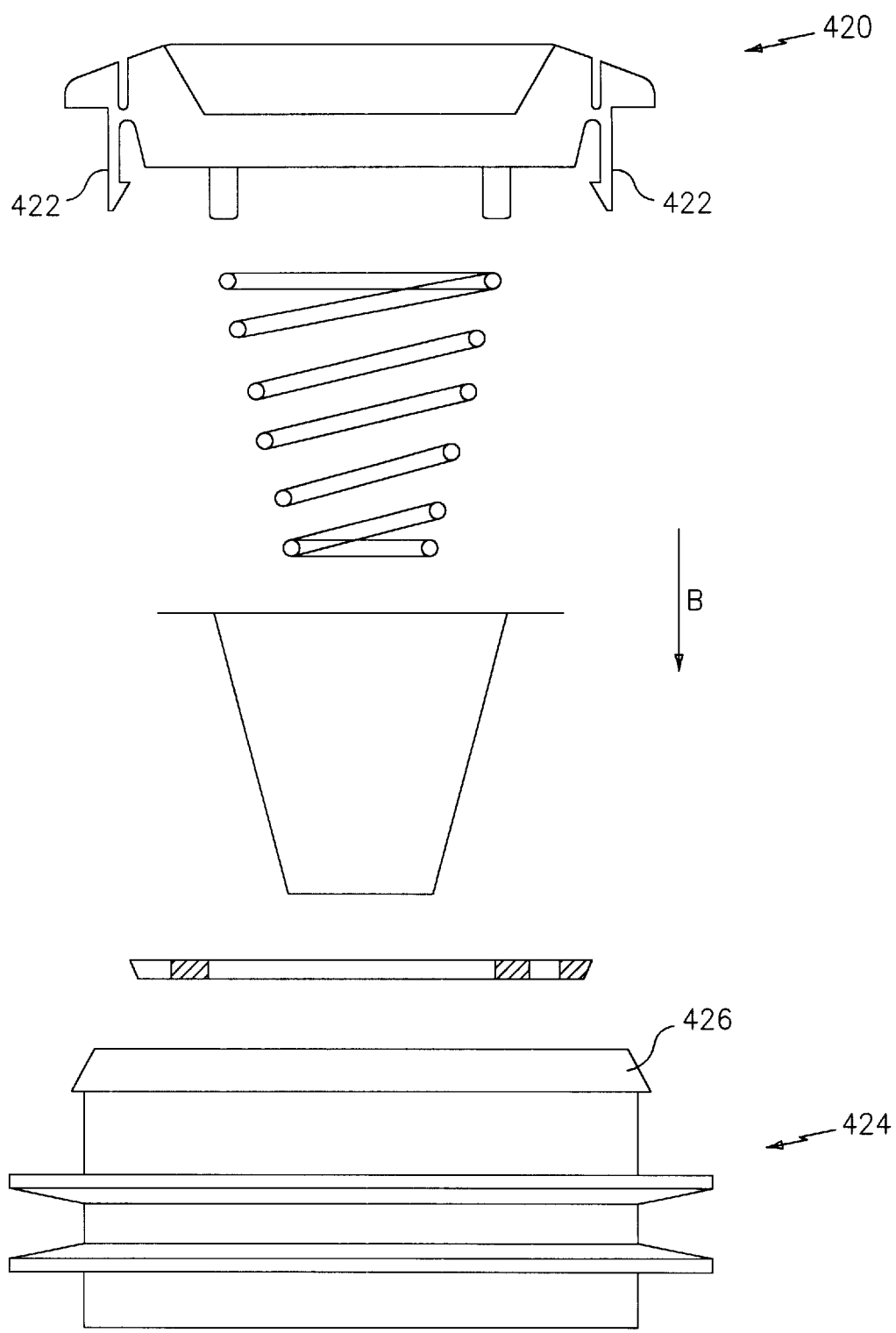
FIG. 25 is an exploded side view of an apparatus for mounting an ultrasound transducer having a cover with external locking structure.

FIGS. 24A and B illustrate an embodiment of insert 400 which has the ability to be raised or lowered within the void in the cast. Insert 400 contains an inner portion 402 and an outer portion 404. Inner portion 402 defines a longitudinal bore therethrough for insertably receiving the several components as discussed above. The outer periphery of inner portion 402 includes a plurality of threads, as indicated by the dashed lines, which engage a corresponding plurality of threads on an inner surface of outer portion 404. The outer periphery of outer portion 404 includes flanges 406, which, as discussed above with reference to FIG. 21, may be secured to cast 410 by weaving a plurality of cast material strips 408 therethrough. Thus, since outer portion 404 will be held in a fixed position adjacent cast 410, rotation of inner portion 402 will adjustably raise or lower the apparatus within the void in cast 410.

Although the illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. An apparatus for mounting an ultrasound transducer head module comprising:
   an insert having an outer surface and an inner surface defining an axial bore therethrough with a proximal inlet and a distal outlet;
   at least one interrupted flange extending radially from said outer surface between the inlet and outlet;
   a spacer configured to fit within a void in a cast, the spacer having an opening therein, the opening having a shape corresponding to an outer periphery of the insert, the insert being at least partially positioned within the opening; and
   means for urgingly biasing an ultrasound treatment head module toward a treatment location, said means positioned adjacent the proximal inlet of the insert; wherein the means for urgingly biasing an ultrasound treatment head module toward the treatment location comprises a housing having a shape corresponding to a shape of the insert, and a bias element mounted on a bottom portion of the housing; wherein the bias element is a conical helical spring.

2. An apparatus for mounting an ultrasound transducer head module as recited in claim 1, wherein the spacer is formed of felt.

3. An apparatus for mounting an ultrasound transducer head module as recited in claim 1, wherein the insert, being at least partially positioned within the hole in the spacer, is supported by the at least one interrupted flange.

4. An apparatus for mounting an ultrasound transducer head module as recited in claim 2, wherein the insert includes at least one circumferential score line to enable the removal of at least one layer of the insert to adjust a height of the insert to correspond to a thickness of a cast.

5. An apparatus for mounting an ultrasound transducer head module as recited in claim 2, further comprising an ultrasound transmission-enhancing medium positioned within the bore of the insert and adjacent a treatment location.

6. An apparatus for mounting an ultrasound transducer head module as recited in claim 5, wherein the ultrasound transmission-enhancing medium is a gel pad.

7. An apparatus for mounting an ultrasound transducer head module as recited in claim 1, wherein the insert includes a hemispherical notch configured to accommodate a cord extending from an ultrasound treatment head module.

8. An apparatus for mounting an ultrasound transducer head module as recited in claim 2, wherein the means for urgingly biasing an ultrasound treatment head module toward the treatment location further comprises an adjustable strap for removably engaging the apparatus with the treatment location.

9. An apparatus for mounting an ultrasound transducer head module as recited in claim 2, wherein the insert is formed of polypropylene.

10. The apparatus of claim 1, wherein the outlet defines a concave surface.

11. An apparatus for mounting an ultrasound transducer head module, comprising:
   an insert having an outer surface and an inner surface defining an axial bore therethrough with a proximal inlet and a distal outlet;
   at least one flange extending radially from said outer surface between the inlet and outlet wherein the flange is a peripherally interrupted flange;
   a cover configured to engage the proximal inlet of the insert and retain the ultrasound transducer head module; and
   locking structure on an outside periphery of said outer surface, said locking structure configured to engage the cover.

12. An apparatus for mounting an ultrasound transducer head module as recited in claim 11, further comprising:
   a spacer configured to fit within a void in a cast, the spacer having an opening therein, the opening having a shape corresponding to a periphery of the insert, the insert being at least partially positioned within the opening.

13. An apparatus for mounting an ultrasound transducer head module as recited in claim 12, wherein the spacer is formed of felt.

14. An apparatus for mounting an ultrasound transducer head module as recited in claim 11, further comprising:
   means for biasing the ultrasound treatment head module positioned within the insert toward a treatment location.

15. An apparatus for mounting an ultrasound transducer head module as recited in claim 11, further comprising an ultrasound transmission-enhancing medium positioned within the insert and adjacent a treatment location.

16. An apparatus for mounting an ultrasound transducer head module as recited in claim 15, wherein the ultrasound transmission-enhancing medium is a gel pad.

17. An apparatus for mounting an ultrasound transducer head module as recited in claim 11, wherein the insert is formed of polypropylene.

18. The apparatus of claim 11, wherein the outlet defines a concave surface.

19. A system for mounting an ultrasound transducer head module comprising:
   an insert having an outer surface and an inner surface defining an axial bore therethrough with a proximal inlet and a distal outlet, said outlet defining a concave plane; wherein the insert is formed of polypropylene;
   at least one interrupted flange extending radially from said outer surface between the inlet and outlet; and
   means for biasing an ultrasound treatment head module positioned within the insert toward an ultrasound transmission-enhancing medium; wherein the means for biasing the-ultrasound treatment head module toward the ultrasound transmission-enhancing medium comprises:
      a housing having a shape corresponding to a shape of the insert and a bias element mounted on a bottom portion of the housing; wherein the bias element is a conical helical spring.

20. A system for mounting an ultrasound transducer head module as recited in claim 19, further comprising:
   an ultrasound transmission-enhancing medium positioned within the bore of the insert and adjacent a treatment location.

21. A system for mounting an ultrasound transducer head module as recited in claim 19, wherein the ultrasound transmission-enhancing medium is a gel pad.

22. A system for mounting an ultrasound transducer head module as recited in claim 19, wherein the means for biasing the ultrasound treatment head module toward the ultrasound transmission-enhancing medium further comprises an adjustable strap for removably engaging the apparatus with the treatment location.

23. An apparatus for mounting an ultrasound transducer head module comprising:

an insert having a first member and a second member;

said first member having an outer surface defining a plurality of strands and an inner surface defining an axial bore therethrough;

said second member having an outer surface and an inner surface defining an axial bore therethrough and having a plurality of threads thereon for threadably receiving said first member, wherein the first member is capable of movement relative to the second member; and at least one interrupted flange extending radially from said outer surface of said second member.

24. A modular, field reconfigurable kit for selectively mounting an ultrasound transducer head module adjacent a treatment location of a body in any one of a pre-cast, post-cast and/or no-cast application, the kit comprising:

an insert having an outer surface and an inner surface defining an axial bore therethrough;

a spacer having an opening which is dimensioned to at least partially receive the insert;

an ultrasound transmission-enhancing medium configured to be positioned between an ultrasound transducer head module and a treatment location;

a cover configured to be positioned within the axial bore of the insert, the cover having means for urgingly biasing an ultrasound treatment head module toward the treatment location;

a strap for engaging an ultrasound transducer head module with the treatment location; and cast material elements.

25. An apparatus for mounting an ultrasound transducer head module comprising:

an insert having an outer surface and an inner surface defining an axial bore therethrough with a proximal inlet and a distal outlet, said outlet defining a concave plane;

at least one interrupted flange extending radially from said outer surface between the inlet and outlet; and a snap plate having an opening therein, the opening having a shape corresponding to an outer periphery of the insert, the insert being at least partially positioned within the opening such that the at least one interrupted flange is positioned adjacent an upper surface of said snap plate.

26. The apparatus for mounting an ultrasound transducer head module as recited in claim 25, wherein the at least one interrupted flange comprises at least one living hinge.

27. The apparatus for mounting an ultrasound transducer head module as recited in claim 26, wherein the at least one living hinge is formed by a reduction in cross-section at a proximal end of the hinge adjacent the axial bore of the insert.

28. The apparatus for mounting an ultrasound transducer head module as recited in claim 25, wherein the snap plate biases the insert in a direction away from a treatment location.

* * * * *